United States Patent [19]

Hettiarachchi et al.

[11] Patent Number: 5,132,093

[45] Date of Patent: Jul. 21, 1992

[54] SYNERGISTIC CORROSION INHIBITORS BASED ON SUBSTITUTED PYRIDINIUM COMPOUNDS

[75] Inventors: Samson Hettiarachchi, Menlo Park; Subhash C. Narang, Redwood City; Digby D. Macdonald, Fremont, all of Calif.

[73] Assignee: SRI International, Menlo Park, Calif.

[21] Appl. No.: 582,796

[22] Filed: Sep. 13, 1990

Related U.S. Application Data

[63] Continuation of Ser. No. 226,432, Jul. 29, 1988, abandoned.

[51] Int. Cl.$^5$ ............................................. C23F 11/00
[52] U.S. Cl. ............................................. 422/7; 422/6; 422/16; 546/304; 546/307; 546/312
[58] Field of Search ............... 546/304, 307, 312; 422/6–7, 16

[56] References Cited

U.S. PATENT DOCUMENTS

| | | | |
|---|---|---|---|
| 3,288,555 | 11/1966 | Napier et al. | 106/14.45 |
| 3,974,220 | 8/1976 | Heib et al. | 564/286 |
| 3,982,894 | 9/1976 | Annand et al. | 252/148 |
| 4,071,746 | 1/1978 | Quinlan | 546/347 |
| 4,100,099 | 7/1978 | Asperger et al. | 252/189 |
| 4,140,853 | 2/1979 | Vorbrueggen | 546/304 |
| 4,212,709 | 7/1980 | Patsch et al. | 546/122 |
| 4,672,118 | 6/1987 | Fisk et al. | 546/14 |

OTHER PUBLICATIONS

Badawi, et al, Chemical Abstracts: 100: 138911n, "Quaternary Ammonium Salts of Potential Biological Activity," (1984).
S. Hettiarachchi, et al., NACE Corrosion '87, Presentation, Mar. (1987).
S. Narang, et al., J. Polym. Sci. Polym. Lett. Ed., vol. 23, p. 147 (1985).
R. Vilceanu, et al.,. Rev. chim. (Bucharest), vol. 32, p. 327 (1981): Chemical Abstracts, vol. 95, 162848w (1981).
S. Hettiarachchi, et al., Proc. 15th International Seminar in Chemical Engineering and Physical Chemistry, University of Karlsruhe, West Germany, Jul. (1980).

*Primary Examiner*—James C. Housel
*Assistant Examiner*—Lyle A. Alexander
*Attorney, Agent, or Firm*—Phillips, Moore, Lempio & Finley

[57] ABSTRACT

The present invention relates to a compound of the formula:

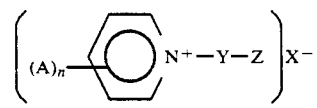

wherein (a) A is independently selected from $-SR^1$, $-NR^1R^2$, $-PR^1R^2$, $-Si,R^1R^2R^3$, or $-SnR^1R^2R^3$, $R^1$, $R^2$ and $R^3$ are each independently selected from alkyl, cycloalkyl, alkylcycloalkyl, arylalkyl having from 1 to 20 carbon atoms or aryl, substituted aryl, or where $R^2$ and $R^3$ together form a heterocycle group, having from 4 to 20 carbon atoms, and n is an integer from 1 to 5;

(b) Y is selected from a direct bond or $-CR^4R^5-$, wherein $R^4$ and $R^5$ are each independently selected from hydrogen, or alkyl group having 1 to 20 carbon atoms or $R^4$ and $R^5$ together form a cycloalkyl group having 4 to 20 carbon atoms;

(c) Z is aryl or substituted aryl; and (d) X is halogen, sulfonate, carboxylate, phosphate, carbonate, sulfate, or $MD_m$ wherein M is boron, phosphorous, arsenic, antimony or silicon, D is fluorine, chlorine, bromine or iodine and m is 2, 3 or 4. These compounds are useful as synergistic corrosion inhibitors for metals. These compounds are also useful as bacteriostats, antifungal agents and as deicing agents as surfactants.

7 Claims, 3 Drawing Sheets

SYNERGISTIC CORROSION INHIBITORS BASED ON SUBSTITUTED PYRIDINIUM COMPOUNDS

This is a continuation, of Ser. No. 226,432, filed Jul. 29, 1988 now abandoned.
.44 PATENT

BACKGROUND OF THE INVENTION

1. Field of the Invention

The present invention relates to novel compounds which are useful as metal corrosion inhibitors. The compounds are N-aryl or N-alkyl substituted pyridinium halides wherein the pyridinium ring itself is further connected to one or more heteroatoms containing alkyl or aryl groups.

2. Description of Related Art

It is known that at high operating temperatures halide ions, such as chloride and bromide ions, are extremely aggressive toward corrosion of many containment materials such as steel, stainless steel, and copper. The type of corrosion exhibited by these metals in strong salty aqueous environments containing oxygen is pitting. Pitting corrosion is one of the most severe types of corrosion. As an example, a single pit penetrating through the containment material in a pressurized system can put the entire system out of action until the damage is repaired. Thus, precautions must be taken beforehand to prevent such failures, which involve direct repair costs as well as downtime costs.

Three basic methods can be used to combat corrosion problems of this nature. These are:

(a) choose a more corrosion-resistant material (which in many cases is economically unattractive);

(b) use a corrosion-resistant coating (which is likely to fail with many commonly used inexpensive coating materials becuase of the temperture cycling involved); and (c) use adsorption type synergistic corrosion inhibitors stable up to 230° C. or higher.

Among these, the use of adsorption-type synergistic corrosion inhibitors appear to be an attractive approach in terms of both effectiveness and cost.

Some general references in this art include:

G. Schmitt, et al., in *Werkstoffe und Korrosion*, Vol. 36, pp. 273-278 published in 1985 disclose some studies relating to structural and electronic effects in acid inhibitors by AC impedance measurements. The acid inhibitors include N-benzyl quinoline derivatives and N-substituted pyridine derivatives. This reference does not teach or suggest the alkylamine-ring substituted pyridines having N-substituted methylnaphthalenes.

D. R. Napier et al. in U.S. Pat. No. 3,288,555 disclose a method of inhibiting corrosion. The inhibitors are prepared by reacting a halomethylated alkyl aromatic compound with a double bonded, conjugated nitrogen compound.

R. P. Annand et al. disclose in U.S. Pat. No. 3,982,894 a method of inhibiting acidic corrosion of ferrous metals with polyquaternary amino polymers.

L. Helb, et al. disclose in U.S. Pat. No. 3,974,220 the use of polymeric quaternary ammonium corrosion inhibitors and petroleum demulsifiers in crude oil refining.

R. G. Asperger et al. in U.S. Pat. No. 4,100,099 disclose quaternary salt-polyamine inhibitors for sour gas conditioning solution used to remove $CO_2$ and $H_2S$ from a gas stream where corrosion is effectively inhibited by a combination of a quaternary pyridinium salt and a lower alkylenepolyamine or corresponding polyalkylenepolyamine.

M. Patsch, et al., in U.S. Pat. No. 4,212,709 disclose an acidic nickel electroplating bath containing sulfobetaines as brighteners or leveling agents. The leveling agents have the formula:

Where only for the purpose of describing these agents in this paragraph, is a heteroaromatic nitrogen base, R, $R^1$ and $R^2$ are hydrogen or aklyl, $R^3$ is arylene, X is $SO_3-$, Y is a neutralizing cation, n is from 1 to 3, and m is from 1 to 2.5.

P. M. Quinlan in U.S. Pat. No. 4,071,746 discloses alkylbenzyl pyridinum compounds of the general formula:

where only for the purposes of describing these agents in this paragraph, R is a hydrocarbon group, occurring n times in the ring and R' is a hydrocarbon group occurring m times and $X^-$ is an anion, preferably halogen. These compositions are employed as corrosion inhibitors preferably in acid systems. They are preferably employed as corrosion inhibitors with surfactants and preferably with surfactants and alcohols.

T. E. Fisk, et al. in U.S. Pat. No. 4,672,118 disclose corrosion inhibitors for metal surfaces in contact with an aqueous medium by incorporating an N-(hydrophobearomatic) pyridinium compound such as N-(p-dodecylphenyl)-2,4,6-trimethyl pyridinium sulfoacetate into the aqueous medium.

Additional references of interest include:

R. Vilceanu, et al., Rev. Chim. (Bucharest), Vol. 32, p. 327 (1981).

S. Hettiarachchi et al., Proc. 15th International Seminar in Chemical Engineering and Physical Chemistry, University of Karlsruhe, West Germany, July (1980).

S. Hettiarachchi, et al., NACE CORROSION '87, Presentation, March (1987).

S. Narang, et al., *J. Polym. Sci. Polym. Lett. Ed.*, Vol. 23, p. 147 (1985).

All of the above references are incorporated herein by reference. None of these references individually or collectively teach or suggest the present invention. It is therefore desirable to have useful synergistic corrosion inhibitors of the structures described herein.

SUMMARY OF THE INVENTION

The present invention relates to a group of N-(alkyl or aryl, or alkaryl) pyridines, wherein the pyridine ring is further ring substituted with specific heteroatom groups. More specifically, the present invention relates to a compound of the formula:

wherein (a) A is independently selected from $-SR^1$, $-NR^1R^2$, $-PR^1R^2$, $-SiR^1R^2R^3$, or $-SnR^1R^2R^3$, $R^1$, $R^2$ and $R^3$ (when present) are each independently selected from alkyl, cycloalkyl, alkylcycloalkyl, arylalkyl having from 1 to 20 carbon atoms or aryl, substituted aryl, or where $R^1$ and $R^2$ together form a heterocycle group, having from 4 to 20 carbon atoms, and n is an integer from 1 to 5;

(b) Y is selected from a direct bond or $-CR^4R^5-$, wherein $R^4$ and $R^5$ are each independently selected from hydrogen, or alkyl groups having 1 to 20 carbon atoms, or $R^4$ and $R^5$ together form a cycloalkyl group having 4 to 20 carbon atoms;

(c) Z is aryl or substituted aryl; and (d) X is halogen, sulfonate, carboxylate, phosphate, carbonate, sulfate or $MD_m$ wherein M is boron, phosphorous, arsenic, antimony or silicon, D is fluorine, chlorine, bromine or iodine and m is 2-6.

Preferred compounds as corrosion inhibitors, etc. are those wherein A is $-NR^1R^2$, n is 1 or 2, Y is $-CH_2-$, Z is naphthyl or X is Cl. Especially preferred are those compounds which combine these moieties.

DETAILED DESCRIPTION OF THE INVENTION AND PREFERRED EMBODIMENTS

Definitions:

As used herein:

"Alkyl" refers to straight or branched chain saturated groups such as methyl, ethyl, n-propyl, n-propyl, n-butyl, i-butyl, t-butyl, pentyl, hexyl, decyl, pentadecyl, octadecyl, cetyl and the like.

"Aryl" refers to benzene, naphthalene, phenanthrane, anthracene and the like having from 6 to 14 carbon atoms.

"Carbonate" refers to $CO_3=$ and the salt obtained by the reaction of one or two organic pyridinium cations with carbonic acid or one of its salts, such as sodium carbonate, or sodium bicarbonate.

"Carboxylate" refers to alkyl or aryl substituted carboxylate, such as acetate, propionate, butyrate, benzoate, naphthalate or the like.

"Halogen" refers to chloride, bromide or iodine. Preferably, it refers to chloride or bromide, especially chloride.

"Heterocycle group" refers to both a cyclic aliphatic group which contains at least one heterocyclic atom, such as oxygen, nitrogen, sulfur, phosphorous, silicon, tin or the like. These groups can be, for example, cyclic amines such as piperdinyl, or pyrrolidinyl cyclic sulfur compounds, cyclic phosphorous compounds, cyclic silicon compounds, or cyclic oxygen compounds. The term may also include heterocyclic aromatic groups where the heteroatom forms a heteroaromatic ring structure. The heteroatom is selected from nitrogen, sulfur, phosphorous, silicon or tin.

"Phosphate" refers to alkyl or aryl phosphates such as methyl phosphate, ethyl phosphate, phenyl phosphate or the like. Phosphate also refers to the salt obtained by the reaction of three organic pyridinium cations with phosphoric acid (or one of its salts).

"Sulfate" refers to $SO_4=$ and to the salt obtained by the reaction of two organic pyridinium cations with sulfuric acid or one of its salts, such as sodium sulfate.

The heteroatoms substituted on the pyridinium ring, such as, provide lone pair electrons to stabilize the aromatic structure and thus stabilize the plus charge on the ring nitrogen of the pyridine structure. The heteroatoms provide stabilization of the plus charge on the nitrogen by an inductive effect on the sigma bond. A key feature of the present invention is the improved effectiveness of these heteroatom substituted pyridinium groups as corrosion inhibitors because of the increased stabilization of the plus charge on the pyridinium nitrogen atom.

"Substituted aryl" refers to an aryl group as defined herein where the aromatic ring is substituted with alkyl groups, or halogen groups, other groups or combinations thereof.

The present invention is concerned with a novel group of synergistic corrosion inhibitors based on N-alkylene aryl substituted quaternary ammonium chlorides, e.g. N-methylenenaphthyl, N-subsituted pyridines or quinolines which are themselves ring substituted with N-nitrogen or S-sulfur, P-phosphorous, Si-silicon, or Sn-tin, substituted alkyl, cycloalkyl or aromatic groups.

Figure 1A:
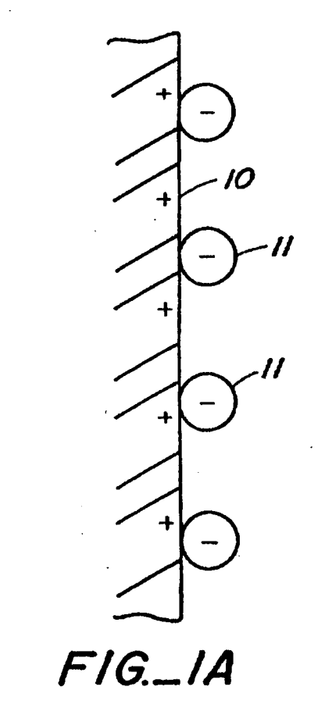
FIG. 1A-1B is a schematic representation of the mechanism of corrosion inhibition of iron in 0.5M $H_2SO_4$ by a synergistic corrosion inhibitor.
Figure 1B:
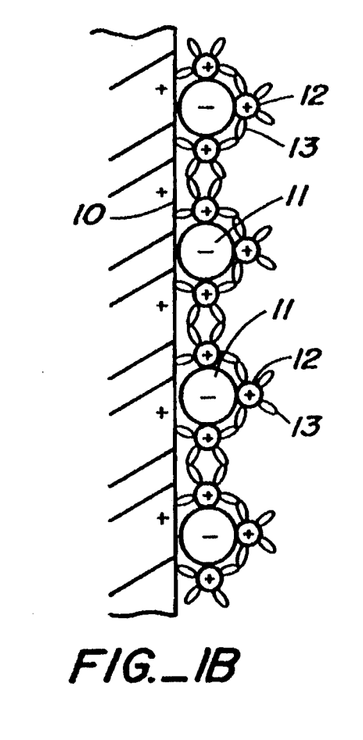

An initial step in the proposed mechanism of inhibiting corrosion using organic compounds is the adsorption of chloride ions on the metal surface. This adsorption, which is often called "specific adsorption," creates an excess negative charge on the metal surface, which in turn attracts the quaternary cations by purely electrostatic forces, as shown in FIG. 1. These adsorbed quaternary cations containing bulky organic groups then cover the metal surface effectively, protecting it from corrosion. The ability to protect the metal from corrosion is largely dependent on the size, structure, electronic, and dielectric properties of the bulky organic groups attached to the quaternary cation.

Figure 2:
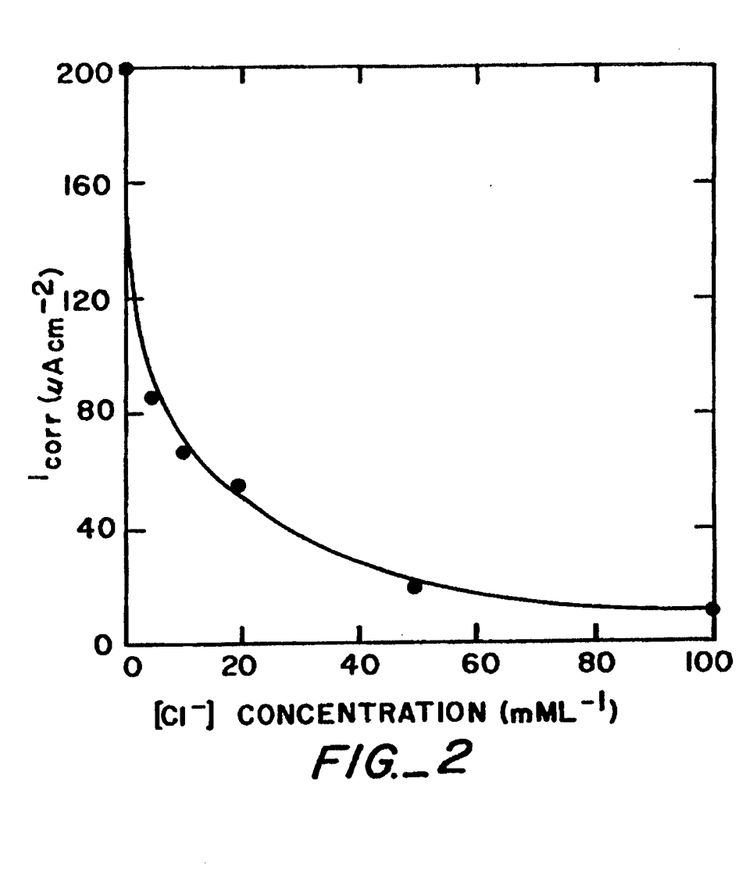
FIG. 2 is a graphic representation of synergistic corrosion inhibition by the added [Cl$^-$] concentration in the presence of a fixed concentration of inhibitor cation.
Figure 3:
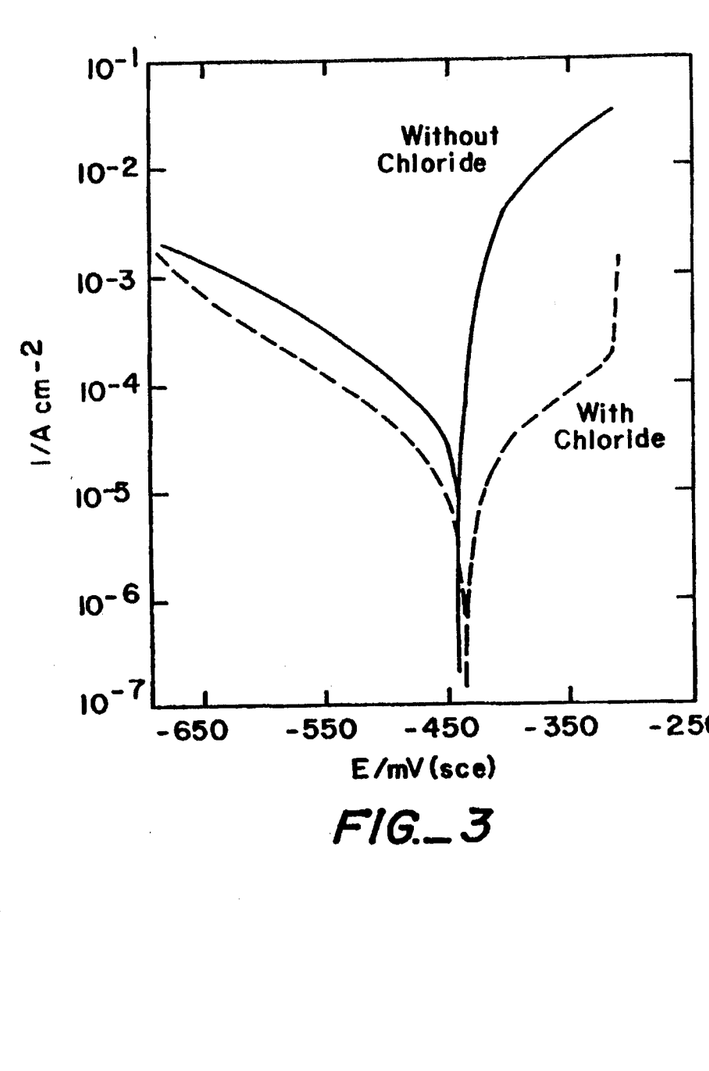
FIG. 3 shows a graphic representation of the polarization curves for mild steel in 0.5 M sulfuric acid showing the ability of chloride ion to promote the inhibiting action of N-methylnaphthyl-4-piperidinopyridinium chloride (NMNPPC).

Because the extent of adsorption of chloride ions depends on the chloride ion concentration in solution, an increasing chloride content inhibits the corrosion of the metal more effectively, as shown in FIG. 2. The synergistic chloride-ion-induced corrosion inhibition is effective even in high chloride-containing solutions, as shown in FIG. 3. Investigations indicate that appropriately substituted quaternary compounds form an excellent group of corrosion inhibitors for large structural applications, even on corroded surfaces. When applied on a corroded surface, these inhibitors reach the metal surface by moving through the corrosion products because of their inherent surfactant properties. In addition, they also have good antibacterial and other properties, thus demonstrating their multifunctionality.

The results of FIGS. 2 and 3 are obtained by using known potentiodynamic polarization studies. The corrosion currents in FIG. 2 are calcluated by extrapolating the anodic and cathodic Tafel slopes to the corrosion potential.

Figure 4:
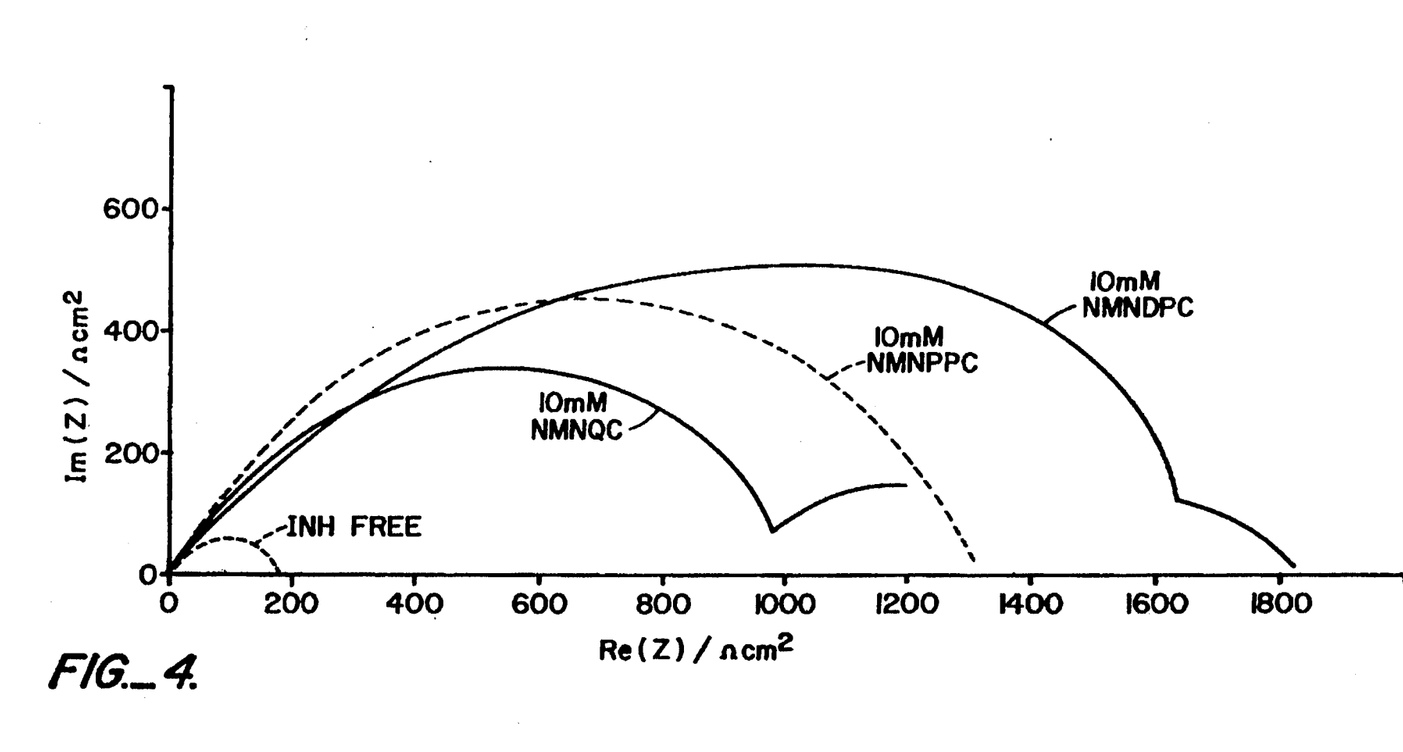
FIG. 4 shows a graphic representation of the effect of stabilizing the positive charge on the quaternary center on corrosion inhibition.
Figure 5:
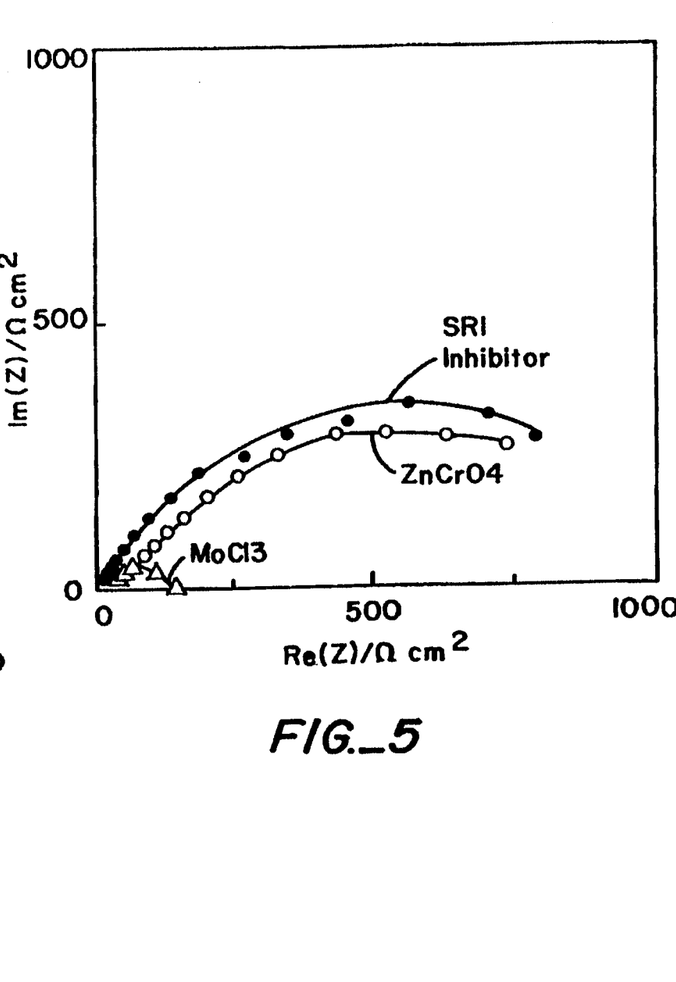
FIG. 5 shows a graphic representation of experiments comparing Nyquist values for zinc chromate and synergistic corrosion inhibitor N-methylnaphthyl 4-N,N-dimethylamino pyridinium chloride (NMNDCP).

FIGS. 4 and 5 are obtained by measuring the interfacial impedence at the metal/solution interface using a Solartron Model 1250 Frequency Response Analyzer produced by Solartron Instruments, Victoria Road, Farnborough, Hampshire, GU14 7PW, England, coupled to a PAR 273 Potentiostat of E G & G, Princeton Applied Research, Princeton, New Jersey. The impedence measurements are performed at the corrosion potential. The difference between the low frequency intercept and the high frequency intercept at the real axis gives the polarization resistance, Rp, which is inversely proportional to the corrosion current.

These techniques are known in this art. Sample references for techniques used herein are: *Electrochemical Corrosion Testing*, edited by F. Mansfeld and U. Bertocci, American Society for Testing and Materials, published in 1979, *Electrochemical Techniques for Corrosion Engineering*, by R. Baboian, ed., National Association of Corrosion Engineers, 1440 South Creek Drive, Houston, Tex. 77084 in 1986, and American Society for Testing and Materials, 1916 Race Street, Philadelphia, Pa. 19103, ASTM Special Technical Publication 727, p. 110–197, which are both incorporated herein by reference.

Preliminary experiments show that quaternary ammonium salts based on N-methytnaphthylpyridinium chloride derived from supernucleophilic pyridines form an excellent group of corrosion inhibitors having synergistic action. FIG. 4 illustrates the effect of two synergistic-type corrosion inhibitors, N-methylnaphthyl-quinolinium chloride (NMNQC) and N-methylnapht-hyl-4-piperidinopyridinium chloride (NMNPPC), in inhibiting the corrosion of steel in 0.5 M $H_2SO_4$ + 10% HCl. Clearly, the $R_p$ values (low frequency intercept of the Nyquist plot) obtained with the inhibitor are much larger than in the absence of the inhibitor. Because the corrosion rate of the metal is inversely proportional to $R_p$, the strongly acid chloride environment containing NMNQC and NMNPPC provides excellent corrosion inhibition to the steel because of the large $R_p$ values of these groups. NMNQC provides an inhibitor efficiency of 85%, whereas NMNPPC provides an efficiency of 89%.

It is also shown that the inhibitors synthesized herein perform better than zinc chromate and considerably better than molybdenum chloride in a solution of 3% NaCl. This is evident from the higher polarization resistance ($R_p$) shown by the SRI inhibitor N-methylnapht-hyl 4-N, N-dimethylaminopyridinium chloride (NMNDPC) (FIG. 5).

The general preparation of the synergistic inhibitors of the present invention is as follows:

To prepare the N-alkylaryl 4-hetero atom substituted pyridinium anion compounds, a halo alkylaryl compound J-Y-Z, is mixed with a heteroatom substituted pyridine (A) N, in a dipolar aprotic solvent, e.g. methylene chloride, chloroform, dimethylformamide, dimethylacetamide or the like. See the following reaction sequence:

The equimolar reagents are then in contact for about 1 to 30 days preferably between about 7 and 21 days at ambient pressure and temperature. The precipitate obtained is recovered by filtration.

In the event that the specific alkyl, aryl (etc.) substituted amino-, phosphorous- , sulfur- , silicon- , or tin- ring substituted pyridine compound is not available, these precursors can be prepared according to methods known in the synthetic art, such as, coupling the alkyl (aryl) heteroatom halide with the corresponding ring substituted lithium pyridine compound.

The preparation of the specific synergistic inhibitors of the present invention is an follows:

(A) To prepare the N-methylnaphthalene 4-amine substituted pyridinium chloride compounds, the 1-chloromethyl naphthalene is mixed with a nitrogen containing ring substituted pyridine in a dipolar aprotic solvent, such as methylene chloride, chloroform, dimethylformamide, dimethylacetamide or the like (Reaction sequence I). The equimolar reagents are then in contact for 1 to 30 days preferably between about 7 and 21 days at ambient pressure and temperature. The precipitate obtained is recovered by filtration.

(NMNDPC)

Preferred compounds prepared by this method include, for example:

(NMNPPC)

(A) To prepare the N-methylnaphthalene 4-diamine substituted compounds of the present invention, 1-chloronaphthalene is mixed with pyridine which has 2-dialkyl (diaryl, etc.) amino groups in a dipolar aprotic solvent as described and recovered as in (A) above (Reaction sequence I')

The disubstituted pyridine is prepared by combining methyl iodine and the 2,5-diaminopyridine. The other derivatives are produced by replacing the diaminopyridine with other diamino, triamino or tetraamino substituted pyridines.

(B) To prepare the N-methylnaphthalene-4-phosphorus substituted pyridinium chloride compounds, the 1chloromethyl naphthalene is mixed with an equimolar amount of the phosphorus containing ring substituted pyridine in a dipolar aprotic solvent. The product precipitates as described above an (A) (Reaction Sequence II).

Preferred compounds prepared by this method include, for example

(C) To prepare the N-methylnaphthalene 4-sulfur alkyl substituted pyridinium chloride, the 1-chloromethylnaphthalene is mixed with an equimolar amount of the sulfur containing ring substituted pyridine in a dipolar aprotic solvent. The product precipitates as is described above in (A) (Reaction Sequence III).

(D) To prepare the N-methylnaphthalene 4-silicon alkyl substituted pyridinium chloride, the 1-chloromethylnaphthalene is mixed with an equimolar amount of the silicon containing ring substituted pyridine in a dipolar aprotic solvent. The product precipitates as is described above in (A) (Reaction Sequence IV).

Preferred compounds prepared by this method include, for example,

Preferred compounds prepared by this method include, for example,

(E) To prepare the N-methylnaphthalene 4-tin alkyl substituted pyridinium chloride, the 1-chloromethylnaphthalene is mixed with an equimolar amount of the tin containing ring substituted pyridine in a dipolar aprotic solvent. The product precipitates as is described above in (A) (Reaction Sequence V).

(V)

Preferred compounds prepared by this method include, for example,

For (A) through (E) above: Ph = φ = phenyl, C-4 to C5 describes an alkylene 4 carbon or 5 carbon ring.

Preferred compounds for the nitrogen, sulfur, phosphorous, silicon or tin heteroatoms is where n is 1 or 2, especially n=1. For n=1 the preferred positions are ortho or para. The para position is especially preferred. For n=2, the ortho and para positions are preferred.

Preferably Y is —$CR^4R^5$—, especially —$CH_2$—.

The above description is for X=Cl⁻. If halogens, i.e. F, Br or I, as salts are desired, the corresponding aryl F, Br, or I is used to react with the corresponding ring substituted pyridinium group. When X is sulfonate, carboxylate, or alkyl or aryl phosphate, these compounds are prepared by loading the desired 'x' group onto a commercial ion exchange resin, and the pyridinium halide is passed over the resin by conventional procedures. The desired salt is then eluted from the ion exchange resin and recovered.

The following examples are to be interpreted as being descriptive and illustrative only. They are not to be construed as being limiting in any way.

The chemical agents, reagents and solvents described herein are usually used as obtained from U.S. chemical supply houses, e.g. Aldrich Chemical Co. (catalogue), Milwaukee, Wisconsin. These and other suitable supply sources can be found in *Chemical Sources — U.S.A.* published annually by Directories Publishing, Inc. of Columbia, S. C., all of which are incorporated herein by reference.

EXAMPLE 1

Synthesis Corrosion Inhibitor A (Amine)

(a) To a 100-ml round bottomed flask is added equimolar amounts of reactants: 3 g of 4-pyrrolidino pyridine (0.0202 moles, Aldrich Chemical Co., Milwaukee, Wisconsin) and 3.58 g of 1-chloromethylnaphthalene (0.0202 moles, Aldrich) dissolved in 50 ml of methylene chloride. The flask is stoppered and allowed to stand for three weeks after which time no further precipitation is observed. The solution is a golden brown color and the solvent is removed by rotary evaporation. The solid dried overnight at 80.C at less than 0.1 torr is identified as the product by infrared spectral analysis.

(b) The process of Example 1(a) is repeated except that the 4-pyrrolidinopyridine is replaced by a stoichiometrically equivalent amount of 4-dimethylamino pyridine from Aldrich Chemical to produce NMNDPC.

(c) The process of Example 1(a) is repeated except that the 4-pyrralidonepyridine is replaced by a stoichiometrically equivalent amount of 4-piperidinopyridine (NMNPPC).

(d) The process of Example 1(a) is repeated except that the 4-pyrralidonepyridine is replaced by a stoichiometrically equivalent amount of 4-diphenylaminopryidine.

(e) The process of Example 1(a) is repeated except that the 4-pyrrolidinopyridine is replaced by a stoichiometrically equivalent amount of 3,5-bis (dimethylamino)pyridine.

(f) The process of Example 1 (a) is repeated except that the 1-chloromethylnaphthalene is replaced by a stoichiometrically equivalent amount of 4-chloromethylanthrancene.

(g) The process of Example 1 (a) is repeated except that the 1-chloromethylnaphthalene is replaced by a stoichiometrically equivalent amount of chloromethylpyrene.

(h) The process of Example 1 (a) is repeated except that the. 1-chloromethylnaphthalene is replaced by a stoichiometrically equivalent amount of benzylchloride.

EXAMPLE 2

Syntheses of Corrosion Inhibitor B (Phosphorous)

(a) The process of Example 1(a) is repeated except that the 4-pyrrolidinopyridine is replaced with a stoichiometrically equivalent amount of 4-pentacyclophosphinpyridine, (b) The process of Example 2(a) is repeated except that the 4-pentacyclophosphinopyridine is replaced by a stoichiometrically equivalent amount of 4-diphenylphosphinopyridine, $\phi_2$-P-pyridine.

(c) The process of Example 2(a) is repeated except that the 4-pentacyclophosphinopyridine is replaced by a stoichiometrically equivalent amount of 4-tributylphosphinopyridine, $(C_4H_9)_3$-P-pryridine.

(d) The process of Example 2(a) is repeated except that the 4-pentacyclophosphinopyridine is replaced by a stoichiometrically equivalent amount of 4-di(cetyl)phosphinylpyridine.

(e) The process of Example 2(a) is repeated except that the 4-pentacyclophosphinopyridine is replaced by a stoichiometrically equivalent amount of 4-didecylphosphinylpyridine.

(f) The process of Example 2(a) is repeated except that the 1-chloromethylnaphthalene is replaced by a stoichiometrically equivalent amount of 4-chloromethylanthracene.

(g) The process of Example 2(a) is repeated except that the 1-chloromethylnaphthalene is replaced by a stoichiometrically equivalent amount of chloromethylpyrene.

(h) The process of Example 2(a) is repeated except that the 1-chloromethylnaphthalene is replaced by a stoichiometrically equivalent amount of benzyl chloride.

EXAMPLE 3

Syntheses of Corrosion Inhibitor C (Sulfur)

(a) The process of Example 1(a) is repeated except that the 4-pyrrolidinopyridine is replaced with a stoichiometrically equivalent amount of 4-methylthiopyridine, $CH_3$-S-pyridine.

(b) The process of Example 3(a) is repeated except that the 4-methylthiopyridine is replaced by a stoichiometrically equivalent amount of 4-phenylthiopyridine.

(c) The process of Example 3(a) is repeated except that the 4-methylthiopyridine is replaced by a stoichiometrically equivalent amount of 4-naphthylthiopyridine.

(d) The process of Example 3(a) is repeated except that the 4-methylthiopyridine is replaced by a stoichiometrically equivalent amount of 4-cetylthiopyridine.

(e) The process of Example 3(a) is repeated except that the 4-methylthiopyridine is replaced by a stoichiometrically equivalent amount of 4-decylthiopyridine.

(f) The process of Example 3(a) is repeated except that the 1-chloromethylnaphthalene is replaced by a stoichiometrically equivalent amount of 4-chloromethylanthracene.

(g) The process of Example 3(a) is repeated except that the 1-chloromethylnaphthalene is replaced by a stoichiometrically equivalent amount of chloromethylpyrene.

(h) The process of Example 3(a) is repeated except that the 1-chloromethylnaphthalene is replaced by a stoichiometrically equivalent amount of benzyl chloride.

EXAMPLE 4

Syntheses of Corrosion Inhibitor D (Silicon)

(a) The process of Example 1(a) is repeated except that the 4-pyrrolidinopyridine is replaced with a stoichiometrically equivalent amount of 4-trimethylsilylpyridine, $(CH_3)_3$-Si-pyridine.

(b) The process of Example 4(a) is repeated except that the 4-trimethylsilylpyridine is replaced by a stoichiometrically equivalent amount of 4-triphenylsilylpyridine.

(c) The process of Example 4(a) is repeated except that the 4-trimethylsilylpyridine is replaced by a stoichiometrically equivalent amount of 4-tributylsilylpyridine.

(d) The process of Example 4(a) is repeated except that the 4-trimethylsilylpyridine is replaced by a stoichiometrically equivalent amount of 4-tricetylsilylpyridine.

(e) The process of Example 4(a) is repeated except that the 4-trimethylsilylpyridine is replaced by a stoichiometrically equivalent amount of 4-tridecylsilylpyridine.

(f) The process of Example 4(a) is repeated except that the 1-chloromethylnaphthalene is replaced by a stoichiometrically equivalent amount of 4-chloromethylanthracene.

(g) The process of Example 4(a) is repeated except that the 1-chloromethylnaphthalene is replaced by a stoichiometrically equivalent amount of chloromethylpyrene.

(h) The process of Example 4(a) is repeated except that the 1-chloromethylnaphthalene is replaced by a stoichiometrically equivalent amount of benzyl chloride.

EXAMPLE 5

Syntheses of Corrosion Inhibitor E (Tin)

(a) The process of Example 1(a) is repeated except that the 4-pyrrolidinopyridine is replaced with a stoichiometrically equivalent amount of 4-trimethyltinpyridine,—(CH₃)₃ Sn-pyridine.

(b) The process of Example 5(a) is repeated except that the 4-trimethyltinpyridine is replaced by a stoichiometrically equivalent amount of 4-triphenyltinpyridine.

(c) The process of Example 5(a) is repeated except that the 4-trimethyltinpyridine is replaced by a stoichiometrically equivalent amount of 4-tributylpyridine.

(d) The process of Example 5(a) is repeated except that the 4-trimethyltinpyridine is replaced by a stoichiometrically equivalent amount of 4-tricetyltinpyridine.

(e) The process of Example 5(a) is repeated except that the 4-trimethyltinpyridine is replaced by a stoichiometrically equivalent amount of 4-tricetyltinpyridine.

(f) The process of Example 5(a) is repeated except that the 1-chloromethylnaphthalene is replaced by a stoichiometrically equivalent amount of 4-chloromethylanthracene.

(g) The process of Example 5(a) is repeated except that the 1-chloromethylnaphthalene is replaced by a stoichiometrically equivalent amount of chloromethylpyrene.

(h) The process of Example 5(a) is repeated except that the 1-chloromethylnaphthalene is replaced by a stoichiometrically equivalent amount of benzyl chloride.

EXAMPLE 6

REPLACING ANIONS X

In Example 1 and 2, the chloride salt is produced. Other X-anions are possible by loading an ion exchange resin with the desired anion, e.g., CH₃(C=O)O—. The pyridinium chloride salt is dissolved in water and/or in a suitable solvent and passed over the resin. The pyridinium acetate is eluted and recovered.

While a few embodiments of the invention have been shown and described herein, it will become apparent to those skilled in the art that various modifications and changes can be made to an alkyl or aryl substituted pyridinium ring itself, such as synergistic corrosion inhibitors further connected to one or more heteroatom containing groups such as N-alkyl(aryl), S-alkyl(aryl), P-alkyl(aryl), Si-alkyl(aryl), or Sn-alkyl(aryl). All modifications and changes herein are considered to be included in the present invention.

We claim:

1. A method of reducing corrosion in a metal, which comprises the step of contacting the metal with synergistic corrosion inhibitors selected from the group consisting of:

-continued and X is halogen, sulfonate, carboxylate, phosphate, or MD$_m$ wherein M is boron, phosphorous, arsenic, antimony or silicon, D is fluorine, chlorine, bromine or iodine, and m is 2 to 6.

2. The method of claim 1 wherein the structure is:

3. The method of claim 1 wherein the structure is:

4. The method of claim 1 wherein the structure is:

5. A method of reducing corrosion in a metal, which comprises the step of contacting the metal with a synergistic corrosion inhibitor selected from the group consisting of:

and X is halogen, sulfonate, carboxylate, phosphate, or $MD_m$ wherein M is boron phosphorous, arsenic, antimony or silicon, D is fluorine, chlorine, bromine or iodine, and m is 2 to 6.

6. The method of claim 5 wherein the structure is

7. The method of claim 5 wherein the structure is:

* * * * *